US 006573285B2

(12) United States Patent
Lebwohl

(10) Patent No.: US 6,573,285 B2
(45) Date of Patent: Jun. 3, 2003

(54) METHOD FOR PREVENTING OR TREATING PAIN BY ADMINISTERING AN ENDOTHELIN ANTAGONIST

(75) Inventor: David E. Lebwohl, Madison, CT (US)

(73) Assignee: Bristol-Myers Squibb Co., Princeton, NJ (US)

( * ) Notice: Subject to any disclaimer, the term of this patent is extended or adjusted under 35 U.S.C. 154(b) by 0 days.

(21) Appl. No.: 10/025,158

(22) Filed: Dec. 19, 2001

(65) Prior Publication Data

US 2002/0082285 A1 Jun. 27, 2002

Related U.S. Application Data

(60) Provisional application No. 60/257,840, filed on Dec. 21, 2000.

(51) Int. Cl.[7] ........................ A61K 31/42; A61K 31/465
(52) U.S. Cl. ........................ 514/365; 514/374; 514/380
(58) Field of Search ................................ 514/365, 374, 514/380

(56) References Cited

U.S. PATENT DOCUMENTS 5,612,359 A * 3/1997 Murugesan .................. 514/365
6,043,265 A * 3/2000 Murugesan et al. ......... 514/374

FOREIGN PATENT DOCUMENTS

| WO | WO 97/21445 | 6/1997 |
| WO | WO 99/56761 | * 11/1999 |
| WO | WO 01/91736 | 12/2001 |

OTHER PUBLICATIONS

Nelson, J.B. et al., BJU International, vol. 85, Supp. 2, pp. 45–48 (Apr. 2000).
Davar, G. et al., Neuroreport, vol. 9, No. 10, pp. 2279–2283 (Jul. 13, 1998).

* cited by examiner

*Primary Examiner*—Frederick Krass
(74) *Attorney, Agent, or Firm*—Stephen B. Davis

(57) ABSTRACT

Prevention or treatment of pain by administration of an endothelin antagonist.

3 Claims, No Drawings

METHOD FOR PREVENTING OR TREATING PAIN BY ADMINISTERING AN ENDOTHELIN ANTAGONIST

This application claims priority to U.S. Provisional Application Serial No. 60/257,840 filed Dec. 21, 2000, the entirety of which is incorporated herein by reference.

FIELD OF THE INVENTION

The present invention relates to the prevention or treatment of pain by administering an endothelin antagonist to a subject in need thereof.

BRIEF DESCRIPTION OF THE INVENTION

Endothelin-1 (ET-1) is a polypeptide with very potent vasoconstrictor activity. Elevated levels ET-1 are found in a variety of diseases including advanced prostate cancer and localized prostate cancer. It has been discovered that ET-1 not only functions as a vasoconstrictor but that it also has other functions, serving, for instance, as a growth factor alone or in combination with other hormones and peptides, as in prostate cancer (see, e.g., *Nature Med.* 1, 944–949, (1995)). In addition, as disclosed in WO 98/46076, ET-1 is related to the sorafotoxins, which are painful and lethal moieties in the venom of certain snakes of the genus Atractapsis. Similar to venom in a snake bite, recombinant ET-1 has been reported to produce intense pain in humans after the localized injection of high concentrations. Thus, for instance, in prostate cancer, a high localized concentration of ET-1 produced by the cancer cells is likely to be a major contributor to the high degree of pain associated with the late stage of the disease. Accordingly, molecules that prevent or inhibit the production of ET-1 can be expected to be useful to prevent and treat pain associated with elevated levels of endothelin.

Endothelin antagonists, which are compounds capable, inter alia, of inhibiting the binding of endothelin peptides to endothelin receptors, are useful in the treatment of endothelin-related disorders. While certain such compounds have been described as having utility in the treatment of hypertension, the present invention provides a method employing these compounds specifically for the treatment of pain.

DETAILED DESCRIPTION OF THE INVENTION

The present invention provides a method for the prevention or treatment of pain associated with elevated levels of endothelin in a mammal, comprising administering an endothelin antagonist to said mammal in an amount effective therefor.

The endothelin antagonist employed may be any compound capable of inhibiting the action of endothelin peptides, especially, endothelin-1 (ET-1), endothelin-2 (ET-2) and/or endothelin-3 (ET-3). The endothelin antagonists described in the following documents, incorporated herein by reference in their entirety, are exemplary of those contemplated for use in the present method: U.S. Pat. No. 5,378,715; U.S. Pat. No. 5,514,696; U.S. Pat. No. 5,420,123; U.S. application Ser. No. 08/114,251, filed Aug. 30, 1993, now U.S. Pat. No. 5,965,732; U.S. application Ser. No. 08/728,238, filed Oct. 8, 1996, now U.S. Pat. No. 6,080,774; European Patent Application 702,012; U.S. application Ser. No. 08/754,715, filed Nov. 21, 1996, now abandoned; U.S. application Ser. No. 08/692,869, filed Jul. 25, 1996, now U.S. Pat. No. 5,780,473; U.S. application Ser. No. 60/011,974, filed Feb. 20, 1996; U.S. application Ser. No. 60/013,491, filed Mar. 12, 1996; U.S. application Ser. No. 60/015,072, filed Apr. 9, 1996; World Patent Application 94/27979; U.S. Pat. No. 5,543,521; U.S. Pat. No. 5,464,853; U.S. Pat. No. 5,514,691; WO 96/06095; WO 95/08550; WO 95/26716; WO 96/11914; WO 95/26360; EP 601386; EP 633259; U.S. Pat. No. 5,292,740; EP 510526; EP 526708; WO 93/25580; WO 93/23404; WO 96/04905; WO 94/21259; GB 2276383; WO 95/03044; EP 617001; U.S. Pat. No. 5,334,598; WO 95/03295; GB 2275926; WO 95/08989; GB 2266890; EP 496452; WO 94/21590; WO 94/21259; GB 2277446; WO 95/13262; WO 96/12706; WO 94/24084; WO 94/25013; U.S. Pat. No. 5,571,821; WO 95/04534; WO 95/04530; WO 94/02474; WO 94/14434; WO 96/07653; WO 93/08799; WO 95/05376; WO 95/12611; DE 4341663; WO 95/15963; WO 95/15944; EP 658548; EP 555537; WO 95/05374; WO 95/05372; U.S. Pat. No. 5,389,620; EP 628569; JP 6256261; WO 94/03483; EP 552417; WO 93/21219; EP 436189; WO 96/11927; JP 6122625; JP 7330622; WO 96/23773; WO 96/33170; WO 96/15109; WO 96/33190; U.S. Pat. No. 5,541,186; WO 96/19459; WO 96/19455; EP 713875; WO 95/26360; WO 96/20177; JP 7133254; WO 96/08486; WO 96/09818; WO 96/08487; WO 96/04905; EP 733626; WO 96/22978; WO 96/08483; JP 8059635; JP 7316188; WO 95/33748; WO 96/30358; U.S. Pat. No. 5,559,105; WO 95/35107; JP 7258098; U.S. Pat. No. 5,482,960; EP 682016; GB 2295616; WO 95/26957; WO 95/33752; EP 743307; and WO 96/31492; such as the following compounds described in the recited documents: BQ-123 (Ihara, M., et al., "Biological Profiles of Highly Potent Novel Endothelin Antagonists Selective for the $ET_A$ Receptor", *Life Sciences*, Vol. 50(4), pp. 247–255 (1992)); PD 156707 (Reynolds, E., et al., "Pharmacological Characterization of PD 156707, an Orally Active $ET_A$ Receptor Antagonist", *The Journal of Pharmacology and Experimental Therapeutics*, Vol. 273(3), pp. 1410–1417 (1995)); L-754,142 (Williams, D. L., et al., "Pharmacology of L-754,142, a Highly Potent, Orally Active, Nonpeptidyl Endothelin Antagonist", *The Journal of Pharmacology and Experimental Therapeutics*, Vol. 275(3), pp. 1518–1526 (1995)); SB 209670 (Ohlstein, E. H., et al., "SB 209670, a rationally designed potent nonpeptide endothelin receptor antagonist", *Proc. Natl. Acad. Sci. USA*, Vol. 91, pp. 8052–8056 (1994)); SB 217242 (Ohlstein, E. H., et al., "Nonpeptide Endothelin Receptor Antagonists. VI:Pharmacological Characterization of SB 217242, A Potent and Highly Bioavailable Endothelin Receptor Antagonist", *The Journal of Pharmacology and Experimental Therapeutics*, Vol. 276(2), pp. 609–615 (1996)); A-127722 (Opgenorth, T. J., et al., "Pharmacological Characterization of A-127722: An Orally Active and Highly Potent $E_{TA}$-Selective Receptor Antagonist", *The Journal of Pharmacology and Experimental Therapeutics*, Vol. 276(2), pp.473–481 (1996)); TAK-044 (Masuda, Y., et al., "Receptor Binding and Antagonist Properties of a Novel Endothelin Receptor Antagonist, TAK-044 {Cyclo [D-α-Aspartyl-3-[(4-Phenylpiperazin-1-yl)Carbonyl]-L-Alanyl-L-α-Aspartyl-D-2-(2-Thienyl) Glycyl-L-Leucyl-D-Tryptophyl]Disodium Salt}, in Human $Endothelin_A$ and $Endothelin_B$ Receptors", *The Journal of Pharmacology and Experimental Therapeutics*, Vol. 279(2), pp. 675–685 (1996)); bosentan (Ro 47–0203, Clozel, M., et al., "Pharmacological Characterization of Bosentan, A New Potent Orally Active Nonpeptide Endothelin Receptor Antagonist", *The Journal of Pharmacology and Experimental Therapeutics*, Vol. 270(1), pp. 228–235 (1994)); and TBC-11251, i.e.:

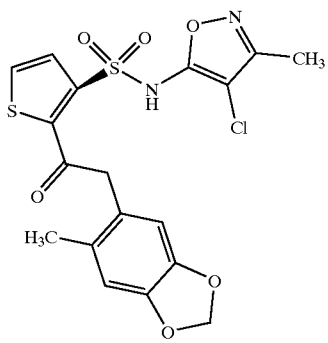

(IBC International Conference on Endothelin Inhibitors, Coronado, Calif. (February 1996) and 211th American Chemical Society National Meeting, New Orleans, La. (March 1996)). These exemplary compounds may, for example, be prepared by methods, and employed at dosages, such as those described in the aforementioned documents.

Endothelin antagonists containing a sulfonamide moiety (—$SO_2$—NH—) are preferred, particularly those described in U.S. Pat. No. 5,612,359. and U.S. Pat. No. 6,043,265. Especially is the following compound:

N-[[2'-[[(4,5-dimethyl-3-isoxazolyl)amino]sulfonyl]-4-(2-oxazolyl[1,1'-biphenyl]-2-yl]methyl]-N,3,3-trimethylbutanamide, having the structure:

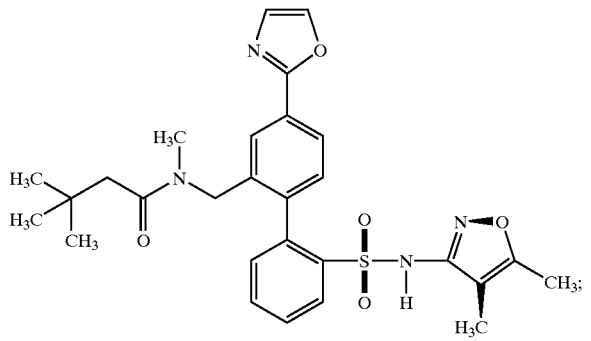

and pharmaceutically acceptable salts thereof. These preferred endothelin antagonists, and particularly the especially preferred compound shown above, are described as having a number of utilities such as the treatment of congestive heart failure and hypertension (see e.g., the disclosures in U.S. Pat. No. 5,612,359 and U.S. application Ser. No. 60/035,832,) wherein the complete recitation of all these utilities is incorporated herein by reference; these preferred endothelin antagonists may be employed for each of these utilities alone or in combination with an agent such as an angiotensin II (AII) receptor antagonist (including irbesartan, 2-n-butyl-4-spirocyclopentane-1-[(2'-(tetrazol-5-yl)biphenyl-4-yl)methyl]-2-imidazolin-5-one).

The mammal may be any mammal subject to this malady, especially, a human. The endothelin antagonist may be administered in any suitable manner such as orally or parenterally, in an effective amount, such as within a dosage range of about 0.1 to about 100 mg/kg, preferably about 0.2 to about 50 mg/kg and more preferably about 0.5 to about 25 mg/kg (or from about 1 to about 2500 mg, preferably from about 5 to about 2000 mg) in single or 2 to 4 divided daily doses.

The present invention also provides pharmaceutical compositions for the prevention or treatment of pain, comprising an endothelin antagonist in an amount effective therefor and a pharmaceutically acceptable vehicle or diluent. The endothelin antagonist can be utilized in a composition such as tablet, capsule, sterile solution or suspension, compounded in a conventional manner with a physiologically acceptable vehicle or carrier, excipient, binder, preservative, stabilizer, flavor, etc. as called for by accepted pharmaceutical practice.

In the methods and compositions of the present invention, the endothelin antagonist may, for example, be employed alone, in combination with one or more other endothelin antagonists, or with another compound or therapies useful for the treatment of pain associated with elevated levels of endothelin, such as narcotics. Additionally, the compounds of the present invention may be employed in combination with typical therapies used in the treatment of cancer, such as radiation therapy, estramustine, CDK inhibitors, antiangiogenic agents (such as MMPI), monoclonal antibodies (such as Herceptin and anti-EGF receptor), 17beta-HSD3 inhibitor, adrenal inhibition (e.g., aminoglutethimide, or ketoconazole), or proapoptic agents (such as retinoids). Additionally, the endothelin antagonists of the present invention may be employed in combination with one or more other compounds useful in the treatment of endothelin-associated disorders. For example, the compounds of this invention can be formulated in combination with endothelin converting enzyme (ECE) inhibitors, such as phosphoramidon; thromboxane receptor antagonists such as ifetroban; potassium channel openers; thrombin inhibitors (e.g., hirudin and the like); growth factor inhibitors such as modulators of PDGF activity; platelet activating factor (PAF) antagonists; anti-platelet agents such as GPIIb/IIIa blockers (e.g., abciximab, eptifibatide, and tirofiban), P2Y(AC) antagonists (e.g., clopidogrel, ticlopidine and CS-747), and aspirin; anticoagulants such as warfarin, low molecular weight heparins such as enoxaparin, Factor VIIa inhibitors, and Factor Xa inhibitors such as those described in U.S. Ser. No. 09/496,571 filed Feb. 2, 2000, now U.S. Pat. No. 6,297,233; renin inhibitors; angiotensin converting enzyme (ACE) inhibitors such as captopril, zofenopril, fosinopril, ceranapril, alacepril, enalapril, delapril, pentopril, quinapril, ramipril, lisinopril and salts of such compounds; neutral endopeptidase (NEP) inhibitors; vasopeptidase inhibitors (dual NEP-ACE inhibitors) such as omapatrilat and gemopatrilat; HMG CoA reductase inhibitors such as pravastatin, lovastatin, atorvastatin, simvastatin, NK-104 (a.k.a. itavastatin, or nisvastatin or nisbastatin) and ZD-4522 (a.k.a. rosuvastatin, or atavastatin or visastatin); squalene synthetase inhibitors; fibrates; bile acid sequestrants such as questran; niacin; anti-atherosclerotic agents such as ACAT inhibitors; MTP inhibitors such as those described in U.S. Ser. No. 09/007,938 filed Jan. 16, 1998; calcium channel blockers such as amlodipine besylate; potassium channel activators; alpha-adrenergic agents, beta-adrenergic agents such as carvedilol and metoprolol; antiarrhythmic agents; diuretics, such as chlorothiazide, hydrochlorothiazide, flumethiazide, hydroflumethiazide, bendroflumethiazide, methylchlorothiazide, trichloromethiazide, polythiazide or benzothiazide as well as ethacrynic acid, tricrynafen, chlorthalidone, furosemide, musolimine, bumetanide, triamterene, amiloride and spironolactone and salts of such compounds; thrombolytic agents such as tissue plasminogen activator (tPA), recombinant tPA, streptokinase, urokinase, prourokinase and anisoylated plasminogen streptokinase activator complex (APSAC); anti-diabetic agents such as biguanides (e.g. metformin), glucosidase inhibitors (e.g., acarbose), insulins, meglitinides (e.g., repaglinide), sulfonylureas (e.g., glimepiride, glyburide, and glipizide), biguanide/glyburide combinations such as those described in U.S. Ser. No. 09/432,465 filed Nov. 3, 1999 and U.S. Ser. No. 09/460,920 filed Dec. 14, 1999; thiozolidinediones (e.g. troglitazone, rosiglitazone and pioglitazone), and PPAR-gamma agonists; mineralocorticoid receptor antagonists such as spironolactone and eplerenone; growth hormone secretagogues such as those described in U.S. Ser. No. 09/417,180 filed Oct. 12, 1999, now U.S. Pat. No. 6,380,184 and U.S. Ser. No. 09/506,749 filed Feb. 18, 2000, now U.S. Pat. No. 6,518,292; aP2 inhibitors such as those described in U.S. Ser. No. 09/391,053 filed Sep. 7, 1999 and U.S. Ser. No. 09/390,275 filed Sep. 7, 1999, now abandoned; digitalis; ouabian; non-steroidal antiinflammatory drugs (NSAIDS) such as aspirin and ibuprofen; phosphodiesterase inhibitors such as PDE III inhibitors (e.g., cilostazol) and PDE V inhibitors (e.g., sildenafil); protein tyrosine kinase inhibitors; antiinflammatories; antiproliferatives such as methotrexate, FK506 (tacrolimus, Prograf), mycophenolate and mofetil; chemotherapeutic agents; immunosuppressants; anticancer agents and cytotoxic agents (e.g., alkylating agents, such as nitrogen mustards, alkyl sulfonates, nitrosoureas, ethylenimines, and triazenes); antimetabolites such as folate antagonists, purine analogues, and pyrimidine analogues; antibiotics, such as anthracyclines, bleomycins, mitomycin, dactinomycin, and plicamycin; enzymes, such as L-asparaginase; farnesyl-protein transferase inhibitors; hormonal agents, such as glucocorticoids (e.g., cortisone), estrogens/antiestrogens, androgens/antiandrogens, progestins, and luteinizing hormone-releasing hormone anatagonists, octreotide acetate; microtubule-disruptor agents, such as ecteinascidins or their analogs and derivatives; microtubule-stabilizing agents such as paclitaxel (Taxol®), docetaxel (Taxotere®), and epothilones A-F or their analogs or derivatives; plant-derived products, such as vinca alkaloids, epipodophyllotoxins, taxanes; and topoisomerase inhibitors; prenyl-protein transferase inhibitors; and miscellaneous agents such as, hydroxyurea, procarbazine, mitotane, hexamethylmelamine, platinum coordination complexes such as cisplatin and carboplatin); cyclosporins; steroids such as prednisone or dexamethasone; gold compounds; cytotoxic drugs such as azathiprine and cyclophosphamide; TNF-alpha inhibitors such as tenidap; anti-TNF antibodies or soluble TNF receptor such as etanercept (Enbrel) rapamycin (sirolimus or Rapamune), leflunimide (Arava); and cyclooxygenase-2 (COX-2) inhibitors such as celecoxib (Celebrex) and rofecoxib (Vioxx).

The effective amount of a compound of the present invention may be determined by one of ordinary skill in the art, and includes exemplary dosage amounts for a human of from about 0.1 to about 100 mg/kg, preferably about 0.2 to about 50 mg/kg and more preferably from about 0.5 to about 25 mg/kg of body weight (or from about 1 to about 2500 mg, preferably from about 5 to about 500 mg) of active compound per day, which may be administered in a single dose or in the form of individual divided doses, such as from 1 to 4 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to endothelin-dependent disorders.

The above other therapeutic agents, when employed in combination with the compounds of the present invention, may be used, for example, in those amounts indicated in the Physicians' Desk Reference (PDR) or as otherwise determined by one of ordinary skill in the art.

The present invention also provides pharmaceutical compositions comprising at least one of the compounds of the formula I capable of treating an endothelin-dependent disorder in an amount effective therefor, and a pharmaceutically acceptable vehicle or diluent. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation or called for by accepted pharmaceutical practice.

The compounds of the formula I may be administered by any suitable means, for example, orally, such as in the form of tablets, capsules, granules or powders; sublingually; buccally; parenterally, such as by subcutaneous, intravenous, intramuscular, or intrastemal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally. For example, the active substance can be utilized in a composition such as tablet, capsule, solution or suspension containing about 5 to about 500 mg per unit dosage of a compound or mixture of compounds of formula I or in topical form for wound healing (0.01 to 5% by weight compound of formula I, 1 to 5 treatments per day). They may be compounded in a conventional manner with a physiologically acceptable vehicle or carrier, excipient, binder, preservative, stabilizer, flavor, etc., or with a topical carrier. The compounds of formula I can also be formulated in compositions such as sterile solutions or suspensions for parenteral administration. About 0.1 to 500 milligrams of a compound of formula I may be compounded with a physiologically acceptable vehicle, carrier, excipient, binder, preservative, stabilizer, etc., in a unit dosage form as called for by accepted pharmaceutical practice. The amount of active substance in these compositions or preparations is preferably such that a suitable dosage in the range indicated is obtained.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene). For example, the compounds of the invention may be administered topically to treat peripheral vascular diseases and as such may be formulated as a cream or ointment.

What is claimed is:

1. A method for preventing or treating pain associated with prostate cancer in a mammal in need thereof, comprising administering to said mammal the compound N-[[2'-[[(4,5-dimethyl-3-isoxazolyl)amino]sulfonyl]-4-(2-oxazolyl)[1,1'-biphenyl]-2-yl]methyl]-N,3,3-trimethylbutanamide or a salt thereof in an amount effective therefor.

2. The method of claim 1, wherein said mammal is a human.

3. A pharmaceutical composition for the prevention or treatment of pain in a mammal, comprising the compound N-[[2'-[[(4,5-dimethyl-3-isoxazolyl)amino]sulfonyl]-4-(2-oxazolyl)[1,1'-biphenyl]-2-yl]methyl]-N,3,3-trimethylbutanamide or a salt thereof in an amount effective therefore in combination with at least one narcotic and a pharmaceutically acceptable vehicle or diluent.

* * * * *